United States Patent
Pearson et al.

(10) Patent No.: US 6,528,040 B1
(45) Date of Patent: Mar. 4, 2003

(54) EMU OIL-BASED FORMULATIONS FOR USE AS AN ANALGESIC, ANESTHETIC AND ANTIPRURITIC

(75) Inventors: Maurine Pearson, 7100 Cross Timbers Rd., Flower Mound, TX (US) 75022; Teresa L. Barr, Port Townsend, WA (US)

(73) Assignee: Maurine Pearson, Pilot Point, TX (US)

( * ) Notice: Subject to any disclaimer, the term of this patent is extended or adjusted under 35 U.S.C. 154(b) by 0 days.

(21) Appl. No.: 09/939,335

(22) Filed: Aug. 24, 2001

Related U.S. Application Data

(60) Provisional application No. 60/262,577, filed on Jan. 18, 2001.

(51) Int. Cl.[7] .................. A01N 25/02; A01N 57/00; A61K 9/00; A61K 31/66; A61K 35/12
(52) U.S. Cl. .................. 424/43; 424/400; 424/520; 424/522; 514/104
(58) Field of Search ................. 424/70.1, 520, 424/522, 93.1, 93.7, 192.1, 198, 43, 400; 435/325; 514/104

(56) References Cited

U.S. PATENT DOCUMENTS

| | | | | |
|---|---|---|---|---|
| 4,837,019 A | * | 6/1989 | Georgalas et al. | 424/101 |
| 5,431,924 A | * | 7/1995 | Ghosh et al. | 424/522 |
| 5,662,921 A | | 9/1997 | Fein | 424/436 |
| 5,958,384 A | | 9/1999 | Holick | 424/60 |
| 6,193,987 B1 | * | 2/2001 | Harbeck | 424/401 |
| 2001/0010813 A1 | * | 8/2001 | Manker et al. | 424/84 |
| 2001/0033838 A1 | * | 10/2001 | Farmer | 424/115 |

* cited by examiner

*Primary Examiner*—David M. Naff
*Assistant Examiner*—Deborah K. Ware
(74) *Attorney, Agent, or Firm*—Buskop Law Group, P.C.; Wendy Buskop

(57) ABSTRACT

An analgesic, anesthetic and antipruritic formulation is provided containing 0.01 to 13 wt % alkyl esters; and 20 to 70 wt % Emu oil; 10 to 33 wt % benzyl alcohol; 10 to 33 wt % benzoin; 0.2 to 2 wt % allantoin; 0.25 to 1.25 wt % methylparaben and 0.01 to 0.30 wt % propylparaben. The formulation may be formulated as a spray or transdermal formula. The formulation may be used for treatment of chronic cutaneous ulcers and burn wounds.

11 Claims, No Drawings

EMU OIL-BASED FORMULATIONS FOR USE AS AN ANALGESIC, ANESTHETIC AND ANTIPRURITIC

The present application claims priority to U.S. Provisional Patent Application Serial No. 60/262,577, filed in the United States Patent and Trademark Office on Jan. 18, 2001.

BACKGROUND OF THE INVENTION

Found in the wild only in Australia, Emus (dromiceius novae-hollandiae) are the second largest members of the ratite group of flightless birds in the world. The Emu have wings but they are very tiny. They can run up to. 35–40 miles an hour, as they have very large and strong legs. Although a very docile creature, the Emu's legs are so strong; one kick can break a man's leg. Now Emus are being farmed in many parts of the world. They are raised for their valuable products, which include very low fat meat, supple leather hides, decorative and nutritional eggs, and very rich oil, which are obtained from the Emu. Emus are by nature, very healthy and immune to many diseases. Emus are referred to a "living dinosaurs," as their skeletal structure closely resembles some dinosaurs. Emus living today closely resemble their ancestors of millions of years ago.

Emu oil, a food by product, is obtained from the fat of the Emu. It is an all-natural substance. When processed, the fat is taken through a series of steps to refine, sterilize and deodorize the oil. Not all Emu oil on the market is refined. Some Emu oil is simply rendered, which means the oil is simply filtered, and may contain contaminants. Emu oil contains high amounts of EFA's (essential fatty acids). EFA's produce energy in the process of oxidation. In humans EFA's govern growth, vitality and mental state of mind. Oxidation is the central and most important living process in our body.

Emu oil by nature is not regarded as a sterile ingredient. Due to lack of regulatory controls and procedures, Emu oil is processed in many different ways, i.e., some forms of rendering, which is simply a filtration process, which leaves the Emu oil with its natural yellow color, and a slight odor. The present invention uses a refinement process, which yields a clearly pure Emu oil product, creamy white and odor free. The present invention utilizes a sterilization technique to render the Emu oil in the present invention free of contaminants to be used as a preparation and treatment for cutaneous wounds and burn ulcers.

Various patents discuss the use of Emu oil, for example, U.S. Pat. No. 5,662,921 discusses how Emu oil can be use to prevent scarring when applied to a newly received cut or burn. It has been known for a long time that Emu oil also diminishes old scars, even stretch marks. Also U.S. Pat. No. 5,662,921 discusses how Emu oil increases high-density lipoproteins, preventing and treating scarring. U.S. Pat. No. 5,958,384 teaches that topical or parenteral administration of Emu oil to a mammal stimulates the proliferation of skin, as well as rejuvenating photo-damaged skin. This same patent teaches that Emu oil also stimulates melannogenesis in the skin and it can be used to treat disorders such as hypopigmentation.

Even so, a need has long existed for a formula, using Emu oil which can be used in hospitals, as a sterile formula for treating of wounds, burns, and other dermatological problems, while remaining stable and usable over time without degradation.

SUMMARY OF THE INVENTION

The present invention comprises a method for treatment of chronic cutaneous ulcers and burn wounds by application of an effective quantity of: alkyl esters; Emu oil; benzyl alcohol; benzoin; allantoin; methylparaben and propylparaben.

The present invention comprises a method for treatment of chronic cutaneous ulcers and burn wounds by application of a quantity of: 0.01 to 13 wt % alkyl esters; 20 to 70 wt % Emu oil; 10 to 33 wt % benzyl alcohol; 10 to 33 wt % benzoin; 0.2 to 2 wt % allantoin; 0.25 to 1.25 wt % methylparaben and 0.01 to 0.30 wt % propylparaben.

The clinical benefits of this formula include reduced wound sepsis rates, improved hempdynamic status, and decreased requirement for donor site harvest. Since engraftment rates are high with good standard care, it is important to evaluate healing outcomes such as durability, functionality, and cosmetic appearance, including scarring. The formula also provides improved quality of healing and products that reduce scarring may also improve function, for example, range of motion, the contour and feel of healed skin, or normalization of skin pigmentation or markings.

The present invention enables tissue to regenerate, restore, and rebuild in the underlying wound itself and surrounding tissue, therefore fortifying, increasing energy to the existing cells that are not necrotic, and fortifying cells that are necrotic. The invention is able to improve wound closure time, and facilitation of surgical closures.

DETAILED DESCRIPTION OF THE PREFFERED EMBODIMENTS

The present invention is an Emu oil based formula that is cable of improved transdermal properties, thus creating healthier cells that proliferate at an accelerated rate. By increasing the feeding of the skin cells, this causes proliferation and thus the theory of Emu oil being biologically active to human skin.

The invention has a preferred formula which contains: Emu oil—20–70 wt %; Benzyl alcohol—10–33 wt %; Benzoin—10–33 wt %; Allatoin 0.2–2.0 wt %; Methylparaben—0.025–1.25 wt %; Alkyl Esters—0.01–13 wt %; and Propylparaben 0.01–0.30 wt %.

The invention based on Emu oil accelerates wound closure, reduces wound debribement, reduces scar tissue and enhances the smoothness and appearance to the skin while maintaining and feeding skin cells with linoleic acid. The invention increases cell proliferation, therefore increasing the ability to heal.

In an alternative embodiment, the present invention can be in the form of a spray having the formula of 63.45% Emu Oil; 20.0% Benzyl Alcohol; 10.0% Benzoic Acid; 1.25% Methylparaben; 0.3% Propylparaben; 2.0% Allantion and 3.0% Alkyl Esters.

The Emu oil, which is most preferred in this invention, has the following chemical analysis:

| | |
|---|---|
| Free Fatty Acid | 0.33–0.02% |
| Acid Value | 0.66% |
| Calculated Iodine value | 69.7–72.8 mEq/100 g |
| OSI | 11.95 Hours @ 110.0 degrees C. |

Wherein the fatty acid composition of the Emu oil can be compared to human skin as follows:

| Emu Oil | | | Human Skin Oil |
|---|---|---|---|
| Myristic | C:14:0 | 0.3% | 2.1% |
| Palmitic | C:16:0 | 20.3% | 20.2% |
| Palmitoleic | C:16:1 | 3.2% | 3.8% |
| Margaric | C:17:0 | 0.2% | |
| Margaric oleic | C:17:1 | 0.1%% | |
| Stearic | C:18:0 | 10.1% | 11.2% |
| Oleic | C:18:1 | 51.6% | 30.8% |
| Linoleic | C:18:2 | 13.1% | 15.1% |
| Linolenic | C:18:3 | 0.5% | 0.3% |
| Arachidic | C:20:0 | 0.1% | |
| Eicosinoac | C:20:1 | 0.5% | |

Other fatty acids, which maybe in Emu oil include elaidic and vaccenic fatty acids.

Analysis of the Emu oil shows calculated iodine content of 72.8%. The present invention embodies the natural iodine properties of the Emu oil. Iodine has long been known for its antiseptic and germicide properties, in turn helping to accelerate wound closure by minimizing infection. Normally, iodine does not occur naturally in nature. In combination as iodides, it is found in the ashes of certain marine algaes and weeds. Until recently, the most important source of iodine was crude Chile saltpeter, and now is been found in the brine of oil wells. Elementary iodine is toxic. The iodine content in the Emu oil is a naturally occurring property, and no reports of toxicity have been noted. The present invention embodies the use of the iodine in the Emu oil as an enhancement to the germicide, fungicide and all around antiseptic properties of the invention. Topical skin dosages of iodine can be used full strength or diluted to 0.1% for applications to wounds. Typically, the therapeutic index for iodine is among the highest of the antiseptics. Unfortunately, iodine burns are common and largely the result of the use of tinctures and solutions with concentrations higher than tolerated by certain skin types. It is the object of the present invention to embody the features, values and benefits of the high iodine content of the Emu oil, in its natural state, and in combination with the Emu oil fatty acid composition, creating a buffer against the harmful side effects of typical iodine.

An analysis of fatty acids in Emu oil reveals that the oil contains approximately 70% unsaturated fatty acids. The major fatty acid found in Emu oil is oleic acid, which is monosaturated and which comprises over 40% of the total fatty acid contents. This fatty acid is a known enhancer for penetration and transportation of compounds through the pores of the epidermis, the membrane of the skin, and, thus, delivering the active ingredients into the lipid layer at the cellular level.

Emu oil also contains both of the two EFA's, which are important to human health and include: 20% linoleic and 1–2% linolenic acid. Essential fatty acid are by definition those fatty acids which we must obtain from our diet since the body cannot manufacture them, hence, making them essential as transdermal supplements to nourish and proliferate new skin cells for chronic cutaneous ulcers and burn wounds. As one can see in the analysis of Emu oil to human skin oil, Emu oil so closely resembles human skin oil; it is a natural food for skin cells.

Emu oil is unique, as most land animals have a higher concentration of saturated fats. Typical fat contains both saturated and unsaturated fatty acids. The fats found in land animals have a higher percentage of side chains than do the fats in sea animals. Although unsaturated fats are less efficient storage sites for food energy because they have fewer CH bonds than do saturated fats, they have a distinct advantage for animals that live in cold water. Saturated fats melt at higher temperatures than do unsaturated fats. In cold waters, sea animals with solid fats would have the reduced ability to move. This theory also subject to analysis, and may be proven easier to transport unsaturated fats through the skin structure and membrane into the lipid layer, rather than a saturated fat.

The monosaturated fatty acid, oleic acid, is the major fatty acid in Emu oil. This fatty acid is a known enhancer for penetration and transportation of compounds through the pores, the membrane of the skin, and, thus, delivering the active ingredients into the lipid layer at the cellular level.

Essential fatty acids (EFA's) play two important roles in human physiology. Both derive from their incorporation into the phospholipids of cell membranes. By virtue of their high degree of unsaturation, and, hence low melting points, they decrease membrane viscosity and affect several aspects of membrane function. Nearly all cells contain basic fat and oil substances. Fats are called energy storehouses, as on a weight-by-weight basis; they contain twice as much energy as a carbohydrate or protein. Fats are also a heterogeneous group of compounds, which are characterized by their solubility in solvents such as ether and therefore insoluble in water. Emu oil is rendered primarily from the fat pads of the bird or from what is referred to as the storage lipids. Emu fat is storage fat, as in most animals and organisms, which mean it is the principal form of stored energy. As an energy source, it is completely combustible to carbon dioxide and water. This releases a quantity of energy similar to the combustion of fossil fuel.

The fats, which are not reactive to sodium or potassium are referred to as unsaponofiable fats. The major portion of unsaponificable fraction is the sterols. These are cholesterol and cholesterol like substances, which have a characteristic chemical composition, which may simply be described as closed ring in contrast to the chain or open ring appearance of the triglycerides and fatty acids. The cholesterol molecule is the classic steroid molecule. This molecule is common to a number of chemicals important to humans, for example, the anti inflammatory steroidal hormones such as hydrocortisone, and androgens such as testosterone, the progestogens, the bile acids, the vitamin D, and estrogen. The restoration of hormonal balance has been attributed to the restoration of many normal functions of the body, as well as general health care and maintenance.

Inflammation is the normal response to healing chronic ulcers and burn wounds. Inflammation also causes scar tissue to form. A product that could decrease wound sensitivity and inflammation, but increase moisture content would be desirable. Adequate lubrication aids the healing process by providing moisture in areas where sebaceous glands are depleted or currently dysfunctional, increasing pliability of the wound area, thus improving pigmentation and vascularity.

The present invention, when topically applied is seen to increase the synthesis of DNA in the epidermis, which is a measure of increase in the proliferative activity of the dermis. It is contemplated that the presence of Oleic acid, a simple triglyceride which contains only one type of fatty acid (oleic acid) enables the present invention to work effectively. A triglyceride is comprised of a glycerin backbone to which the fatty acids are attached. Naturally occurring triglycerides usually are mixed triglycerides; i.e., they contain more than one fatty acid. An example of a mixed triglyceride is palmmitodiolein, the fatty acid composition of which is, as the name indicates, one molecule of palmitic acid and two molecules of oleic acid. This triglyceride may have structural arrangements other than the one shown, i.e., the fatty acid molecules may be arranged with palmitic acid occupying any of the two possible different positions. Oleic acid is also a monosaturated fat.

Linoleic acid is an essential polyunsaturated fatty acid. Linoleic acid deficiency symptoms include scaly skin and slow to heal wounds. Linoleic acid supplementation may be essential and crucial to fortify slow to heal wounds and strengthen and rebuild the skin by increasing linoleic acid content through the membrane and into the lipid layer, thus allowing and enhancing new skin cell and membrane proliferation, as well as minimizing scar tissue. Linoleic acid is required for the formation and maintenance of the epidermal barrier. The present invention requires linoleic acid.

Stearic acid is also called octadecanoic acid, one of the most common long chain fatty acids, found in combined form in natural animal and vegetable fats. Commercial stearic acid is a mixture of approximately equal amounts of stearic and palmitic acids and small amounts of oleic acid. In nature stearic acid occurs primarily as a mixed triglyceride, or fat, with other long-chain acids and as an ester of fatty alcohol. It is much more abundant in animal fat than in vegetable fat; lard and tallow often contain up to 30 percent stearic acid. Stearic acid is a natural component of the present invention.

The composition and structure of the fatty acids of the naturally occurring lipids have an even number of carbon atoms because they are synthesized from acetyl groups, each of which contains two carbon atoms. Fatty acids with 16 (palmitic acid) and 18 (stearic acid) carbon atoms are most commonly found in nature, but the reason for their abundance have not yet been established. Fatty acids constitute important components of lipids in plants, animals and microorganisms. In most cases, they are not found in free form, but instead are bound to other compounds to form fatty acid containing lipid, e.g., neutral lipids (triglycerides) sterols, phosphoglycerides such as lecithin, and sphingolipids such as sphingomyelin. Two typical fatty acids are oleic and palmitic. Although palmitic acid and stearic acid are the major saturated fatty acids found in animal and plant tissues, significant amounts of other saturated fatty acids such as myristic acid and lauric acid, occur in certain tissues, and lignoceric acid and behenic acid are found in high concentrations in brain sphingolipids. Small amounts of fatty acids with an odd number of carbon atoms are also known, e.g., pentadecanoic acid and heptadeconoic acid.

The present invention includes linoleic acid which when transferred to the lipid layer may be crucial to "feeding" the skin cells, creating more energy to burn, thus enhancing skin and membrane cell proliferation and fortification, thus reducing scar tissue as well.

Linoleic acid is required for the formation and maintenance of the epidermal barrier.

Emu oil has been used in many preparations over the years for all types of skin complaints and maintenance. It has been noted that Emu oil has a positive effect on chronic cutaneous ulcers and burn wounds. Because a wound represents a breach in the body's natural barrier to microbial invasion, the final formulation of topical products used for the treatment of chronic cutaneous ulcers and burn wounds should be sterile to avoid introducing exogenus microorganisms. With this in mind, a product that could be sterilized for chronic cutaneous ulcers and burn wounds that could contain a high amount of Emu oil would be favorable for the industry. With respect to wounds in general, a spray product would be favorable to avoid touching sensitive areas associated with chronic cutaneous ulcers and burn wounds.

It is within the scope of the present invention to use the formulation for chronic cutaneous ulcers, which also includes and addresses venous stasis ulcers, diabetic foot ulcer, pressure ulcers, graft sites, donor sites and burn wounds. The present invention is contemplated as a sterile formulation. The guidance on validation of the manufacture of sterile products can be found in the FDA's submission Documentation for Sterilization Process Validation for Human and Veterinary Drug Products (November 1994), which is hereby incorporated by reference.

The present formulation is usable to reduce debridement on tissue. It is generally accepted that necrotic tissue inhibits wound healing by interfering with tissue repair and promoting microbial growth. Thorough debridement of wounds is therefore considered standard care essential to healing.

The unique formulation can be used in wound pain control.

The invention relates to a spray on product, which is sterilized, a germicide, a bateriacide, an antiseptic, an antifungal, and a bateriastatic agent. If a spray on is used, it can be the preferred embodiment, plus any additional environmentally friendly propellants.

It is conceived that this formula can be modified to that it is prepared in the form of a gel, a cream, a lotion, a spray, a patch, or an enhanced oil.

The present invention has a formulation, which additionally inhibits the adverse of affects and allergic reactions to benzoin derivatives.

The present invention consists of Emu oil as a transdermal facilitator and other components that acts to provide effective transport across the dermis or mucous membranes. This component reduces necrotic tissue, to reduce infection, fight the infection that is in tissue, and keep tissue from growing fungus, or going into sepsis. The Emu oil and components also act as an anti-inflammatory agent.

The present invention can include analgesic, anesthetic, and anti-puritic ingredients.

The present invention can additionally contain antimicrobial agents for wound infection control, a topical anti-infective, and elimination of microbial growth and necrotic tissue, which interferes with tissue repair. In addition, the formula can include a topical analgesic/anesthetic at active levels (as set by FDA,) and act as a topical pain control product.

The active ingredients of the product may consist of any of the following, within the established concentration for each ingredient: Emu oil 20–70 wt %, but most preferably 60–65 wt %.

Benzyl Alcohol can be added in weight percents ranging from 10 to 33 percent. The most preferred formulation utilizes 20.0 wt % benzyl alcohol.

Benzyl alcohol is listed in a summary of ingredient categories and testing as a category 1 analgesic, anesthetic, and anti-puritic active ingredient. One example of usable benzyl alcohol is Benzyl Alcohol NF-Benzenemethanol; Phenylcarbinol $CH_2$-OH Benzyl Alcohol $C_7 H8°$. The benzyl alcohol, which can be used within the scope of the invention, involves using esters of benzoic and cinnamic acids in storax, Peruvian balsam, and tolu balsam. A product currently on the market can be used which is made synthetically from benzyl chloride by distilling it from an aqueous solution of potassium carbonate with thorough agitation.

The present invention also relates to use of the formula as a local anesthetic by injection and by application to mucous membranes. Externally the formula can be applied as an ointment or as a lotion in topical preparations and used as a bacteriastatic agent in various parenteral preparations. Externally the formula can also be applied to nasal passages and gum tissues.

The formulation may further include an aromatic alcohol, in amounts from 0.5 to 1.2 wt %, which can be used in a concentration of 0.9% as a bacteriastatic preservative in multiple dose vials of solution or drugs for parenteral therapy. An aromatic alcohol such as Benzyl Alcohol can be used.

Various antimicrobial drugs can be added to the Emu oil, including but not limited to: methylparaban or a benzoic acid, or an alkyl ester such as 4-hydroxy-, methyl ester; or possibly Solbrol made by Charkit Chemical Corporation, P.O. Box 1725, Darien, Conn. 07407; Methyl Parasept made by Charkit Chemical Corporation, P.O. Box 1725, Darien, Conn. 07407; Nipagin or even a Methyl p-hydroxybenzoate (99-76-3) C8 H8 O3 An antimicrobial additive can be formed by esterifying para-hydroxybenzoic acid with methanol using known techniques. The para-hydroxybenzioc acid is obtained by passing carbon dioxide under pressure into dry potassium phenolate heated to about 200 degrees. The resulting potassium salt is decomposed with HCI yielding the free parabic acid. These components can be added in amounts ranging from 0.25–1.25 wt % and most preferably, 2.5 wt %.

Additional preservatives can be added to the inventive formula such as Imidazolidinyl Urea in concentrations ranging from 0.05 to 1.0%.

Methylparabens and other related esters are of para-hydroxybenzoic acid which are odorless and harmless to the skin can be employed in the formula. A combination of two or more esters of para-hydroxybenzoic acid has a "synergistic" antiseptic value, i.e. the antiseptic effect of the combination is greater than the total effect as calculated from the values of the individual components; thus a preparation containing 0.15% of the propyl ester (propylparaben) and 0.05%of the benzyl ester has a stronger antiseptic value than 0.2% of either ester alone. The benzyl ester has a high antiseptic value and is suitable for the preparation of antiseptic creams. The preferred amount of alkyl ester for use in the invention is between 1–13 wt % and most preferably 3.0 wt %.

Parahydroxybenzoic acid esters and mixtures of methylparaben and propylparaben can be used in the invention with excellent and unexpected results. They are commonly used as antimicrobial preservatives; and the amount of their use is contemplated to be in ranges of methylparaben 0.025–0.2 wt percent, with a preferred range of 0.1 to 01.25% and propylparaben in the range of 0.01 to 0.4 wt %, most preferably, approximately 0.3%–0.04 wt %.

Specific benzoic acids having between 12 and 15 carbon atoms, and alkyl esters can be added to an embodiment for the formula. For example, flowers of Benzoin; flowers of Benjamin; Phenylformic Acid, and Benzoic Acid, which is $C_7H_6O_2$, can be used. Benzoic Acid is the simplest acid of the aromatic series. Although the acid is of minor significance as a medicinal agent, it derivatives and salts constitute an important group of valuable medical agents. The addition of this component to the formula, enable the invention to act as an antifungal agent chiefly in combination with salicylic acid as well as being an anesthetic. When the Emu oil contains enough benzoic acid it can then be used in the treatment of athletes' feet and to a lesser extent in the management of ringworm, for humans and animals. Benzoin is preferably used in amounts between 10–33 wt % and most preferably 10 wt %.

Still another ingredient, Allantoin can be used, specifically, Allantoin-5-Ureidohydantoin $C_4H_6N_4O_3$ can be added to the formula. Allantoin is used topically as a vulnerary to stimulate tissue repair in suppurating wounds, resistant ulcers, acne seborrhea, and basic dermatological infections. It is also included in some topical preparations for oral and dental use. It is frequently combined with antiseptics and antifungal drugs. The silver salt is used in the topical treatment of extensive burns. Typically, 0.2 to 2.0% of this ingredient can be used. in the formula, particularly when the invention is used as creams, lotions or shampoo.

The formula of this invention uniquely can be sterilized. Traditionally, sterilization has broken down the components of oils, which contain these types of fatty acids. The objective of a sterilization process is to remove or destroy all microorganisms in or on a preparation and to assure in this way the preparation is free of infectious hazards when used with a patient. Since the variety and amounts of the variety and amounts of sterile materials required for health care have increased in significant proportions, sterilization technology has become increasingly important. Alternatively, if sterilization of the oil is not preferred, then a disinfectant can be added to the formula to render the skin noninfectious. A usable disinfectant may be an antiseptic or a germicide.

The best formula for the present invention has the following components. The ranges for each component are in weight percent of the entire composition, and are as follows:

| | |
|---|---|
| Emu oil | 63.5% |
| Benzyl alcohol | 20.0% |
| Benzoin | 10.0% |
| Allantoin | 2.0% |
| Methyl paraben | 1.25% |
| Alkyl esters | 3.0% |
| Propylparaben | 0.04% |

The present invention contemplates a method for obtaining complete wound closure for chronic, non-healing wounds using the formulation comprising: 0.01 to 13 wt % alkyl esters; and 20 to 70 wt % Emu oil; 10 to 33 wt % benzyl alcohol; 10 to 33 wt % benzoin; 0.2 to 2 wt % allantoin; 0.25 to 1.25 wt % methylparaben and 0.01 to 0.30 wt % propylparaben.

The present invention contemplates a method for accelerating wound closure by diminishing the time required to obtain complete wound closure by using the formulation comprising: 0.01 to 13 wt % alkyl esters; and 20 to 70 wt % Emu oil; 10 to 33 wt % benzyl alcohol; 10 to 33 wt % benzoin; 0.2 to 2 wt % allantoin; 0.25 to 1.25 wt % methylparaben and 0.01 to 0.30 wt % propylparaben.

The present invention contemplates a method for accelerating the healing of burns and donor site wounds, using the formulation comprising: 0.01 to 13 wt % alkyl esters; and 20 to 70 wt % Emu oil; 10 to 33 wt % benzyl alcohol; 10 to 33 wt % benzoin; 0.2 to 2 wt % allantoin; 0.25 to 1.25 wt % methylparaben and 0.01 to 0.30 wt % propylparaben.

The present invention contemplates a method for controlling wound infections using a topical anti-infective formula using the formulation comprising: 0.01 to 13 wt % alkyl esters; and 20 to 70 wt % Emu oil; 10 to 33 wt % benzyl alcohol; 10 to 33 wt % benzoin; 0.2 to 2 wt % allantoin; 0.25 to 1.25 wt % methylparaben and 0.01 to 0.30 wt % propylparaben.

The present invention contemplates a method for controlling irritants on the skin using the formulation comprising: 0.01 to 13 wt % alkyl esters; and 20 to 70 wt % Emu oil; 10 to 33 wt % benzyl alcohol; 10 to 33 wt % benzoin; 0.2 to 2 wt % allantoin; 0.25 to 1.25 wt % methylparaben and 0.01 to 0.30 wt % propylparaben.

The present invention contemplates a method for healing skin ulcers, venous stasis and diabetic ulcers using the formulation comprising: 0.01 to 13 wt % alkyl esters; and 20 to 70 wt % Emu oil; 10 to 33 wt % benzyl alcohol; 10 to 33 wt % benzoin; 0.2 to 2 wt % allantoin; 0.25 to 1.25 wt % methylparaben and 0.01 to 0.30 wt % propylparaben.

The present invention also contemplates a spray on transdermal formula having the additional transdermal effect of promoting the transdermal delivery of additional antiseptic, antifungal, and pain relieving medicine by proliferating new skin cell growth and development, comprising: 0.01 to 13 wt % alkyl esters; and 20 to 70 wt % Emu oil; 10 to 33 wt % benzyl alcohol; 10 to 33 wt % benzoin; 0.2 to 2 wt % allantoin; 0.25 to 1.25 wt % methylparaben; 0.01 to 0.30 wt % propylparaben; and sufficient and effective amounts of environmentally safe propellants.

The invention may be embodied in many forms without departing from the spirit or essential characteristics of the invention.

The present embodiments are therefore to be considered in all respects as illustrative and not restrictive, the scope of the invention being indicated by the appended claims rather than by the foregoing description. All changes, which come within the meaning and range of equivalency of the claims, are therefore intended to be embraced therein.

What is claimed is:

1. An analgesic, anesthetic and antipruritic formulation comprising:

0.01 to 13 wt % alkyl esters;

20 to 70 wt. % Emu oil;

10 to 33 wt % benzyl alcohol;

10 to 33 wt % benzoin;

0.2 to 2 wt % allantoin 0.25 to 1.25 wt % methylparaben; and 0.01 to 0.30 wt % propylparaben.

2. The formulation of claim 1, comprising 60–65 wt % refined and sterilized Emu oil.

3. The formulation of claim 2, wherein said refined and sterilized Emu oil comprises at least 70 wt % linoleic and linolenic acids in combination.

4. The formulation of claim 3, wherein said formulation comprises 20 wt % linoleic and 1–2 wt % linolenic acid.

5. The formulation of claim 1, comprising 10 to 20 wt % benzyl alcohol.

6. The formulation of claim 1, wherein said benzyl alcohol is selected from the group consisting of NF Benzenemethanol, phenyl carbinol $CH_2OH$, and Benzyl $C_7H_8$.

7. The formulation of claim 1, wherein said formulation is a topical treatment for the epidermis.

8. The formulation of claim 1, wherein said formulation can be applied to horses and humans.

9. The formulation of claim 1, further comprising a member selected from the group consisting of a germicide, a bacteriacide, an antiseptic, an antifungal, a bacteriastatic agent and combinations thereof.

10. The formulation of claim 1 prepared in the form of a gel, a lotion, a spray, a patch or an enhanced oil.

11. An analgesic, anesthetic and antipruritic spray-on transdermal formula comprising:

0.01 to 13 wt % alkyl esters;

20 to 70 wt % refined and sterilized Emu oil;

10 to 33 wt % benzyl alcohol;

10 to 33 wt % benzoin;

0.2 to 2 wt % allantoin;

0.25 to 1.25 wt % methylparaben;

0.01 to 0.30 wt % propylparaben; and sufficient and effective amounts of environmentally safe propellants.

* * * * *